United States Patent [19]

Gortz

[11] Patent Number: 4,702,397
[45] Date of Patent: Oct. 27, 1987

[54] PRESSURIZED FLUID DISPENSER

[75] Inventor: Norman Gortz, Newport Beach, Calif.

[73] Assignee: Infusion Systems Corporation, Irvine, Calif.

[21] Appl. No.: 651,835

[22] Filed: Sep. 18, 1984

[51] Int. Cl.⁴ ..................... B65D 37/00; A61M 5/005
[52] U.S. Cl. .................................. 222/211; 222/212;
222/213; 222/214; 222/464; 222/547;
222/386.5; 604/250
[58] Field of Search ............... 222/212, 209, 206, 215,
222/211, 214, 386.5, 105, 464, 564, 547, 95, 450;
251/122, 903; 604/250

[56] References Cited

U.S. PATENT DOCUMENTS

| | | | |
|---|---|---|---|
| 2,397,455 | 3/1946 | Chmielowiec | 299/85 |
| 2,506,035 | 5/1950 | Parker | 120/42.4 |
| 2,761,445 | 9/1956 | Cherkin | 128/214 |
| 2,816,690 | 12/1957 | Lari | 222/92 |
| 2,855,933 | 10/1958 | Erikson | 128/272 |
| 2,876,768 | 3/1959 | Schultz | 128/214 |
| 2,882,543 | 4/1959 | Revero | 15/138 |
| 2,966,282 | 12/1960 | Geisler | 222/95 |
| 3,032,037 | 5/1962 | Huber | 128/276 |
| 3,048,171 | 8/1962 | Grau | 128/214 |
| 3,208,646 | 9/1965 | Wessenger | 222/386.5 |
| 3,339,809 | 9/1967 | Church | 222/215 |
| 3,361,303 | 1/1968 | Jacuzzi | 222/183 |
| 3,371,824 | 3/1968 | Goss | 222/105 |
| 3,412,900 | 11/1968 | Macaulay | 222/82 |
| 3,412,906 | 11/1968 | Dinger | 222/183 |
| 3,468,308 | 9/1969 | Bierman | 128/214 |
| 3,469,578 | 9/1969 | Bierman | 222/215 X |
| 3,486,539 | 12/1969 | Jacuzzi | 141/329 |
| 3,496,937 | 2/1970 | Balson | 128/216 |
| 3,506,005 | 4/1970 | Gilio et al. | 128/214 |
| 3,552,604 | 1/1971 | Gordon | 222/95 |
| 3,672,543 | 6/1972 | Roper et al. | 222/183 |
| 3,677,444 | 8/1972 | Merrill | 222/135 |
| 3,698,595 | 10/1972 | Gortz | 220/63 |
| 3,738,538 | 6/1973 | Roper et al. | 222/183 |
| 3,767,078 | 10/1973 | Gortz et al. | 222/386.5 X |
| 3,791,557 | 2/1974 | Venus | 222/105 |
| 3,796,356 | 3/1974 | Venus | 222/212 |
| 3,817,248 | 6/1974 | Buckles | 128/260 |
| 3,831,600 | 8/1974 | Yum et al. | 128/214 |
| 3,876,115 | 4/1975 | Venus et al. | 222/183 |
| 3,895,631 | 7/1975 | Buckles et al. | 128/213 |
| 3,895,741 | 7/1975 | Nugent | 222/103 |
| 3,907,169 | 9/1975 | Gortz | 222/95 |
| 3,940,026 | 2/1976 | Kain | 222/212 |
| 3,961,725 | 6/1976 | Clark | 222/1 |
| 3,981,415 | 9/1976 | Fowler et al. | 222/95 |
| 3,993,069 | 11/1976 | Buckles et al. | 128/214 |
| 4,140,117 | 2/1979 | Buckles et al. | 128/213 |
| 4,201,207 | 5/1980 | Buckles et al. | 128/214 |
| 4,222,499 | 9/1980 | Lee | 222/183 |
| 4,299,222 | 11/1981 | Eckenhoff | 128/278 |
| 4,314,567 | 2/1982 | Cannon | 128/214 |
| 4,318,400 | 3/1982 | Perry | 128/214 |
| 4,324,350 | 4/1982 | Thompson | 222/212 |

(List continued on next page.)

FOREIGN PATENT DOCUMENTS 489110  12/1952  Canada .

Primary Examiner—H. Grant Skaggs
Assistant Examiner—Gregory L. Huson
Attorney, Agent, or Firm—Knobbe, Martens, Olson & Bear

[57] ABSTRACT

A dispenser for fluids includes an elastic bladder having an open end and a closed end and includes a bladder mounting structure for maintaining the bladder in tension. The bladder mounting structure includes a fixed structural element having a convex curved surface. The mounting structure also includes mounting elements for fixing the two ends of the bladder relative the curved surface so that bladder is stretched over the curved surface. A flow controller communicates with the open end of the bladder to regulate the flow of fluid from the bladder. The flow controller includes a body having a fluid flow path through it. A shutoff element in the fluid flow path controls the cross-sectional flow area of the flow path. Movement of the shutoff element is controlled by a mechanism sealed from the fluid flow path.

13 Claims, 10 Drawing Figures

U.S. PATENT DOCUMENTS

| | | | |
|---|---|---|---|
| 4,335,835 | 6/1982 | Beigler et al. | 222/95 |
| 4,345,594 | 8/1982 | Bieera et al. | 128/214 |
| 4,347,953 | 9/1982 | Bauer | 222/207 |
| 4,349,129 | 9/1982 | Amnous | 222/41 |
| 4,358,026 | 11/1982 | Makinon | 222/1 |
| 4,376,500 | 3/1983 | Banks et al. | 222/306 |
| 4,379,453 | 4/1983 | Baroa | 604/145 |
| 4,386,717 | 6/1983 | Koob | 222/94 |
| 4,386,929 | 6/1983 | Perry et al. | 604/132 |
| 4,419,096 | 12/1983 | Leeper et al. | 604/132 |
| 4,423,829 | 1/1984 | Katz | 222/95 |
| 4,431,009 | 2/1984 | Marino, Jr. et al. | 128/673 |
| 4,446,991 | 5/1984 | Thompson | 222/94 |
| 4,493,438 | 1/1985 | Rutter | 222/83 |
| 4,539,005 | 9/1985 | Greenblatt | 604/141 |
| 4,573,977 | 3/1986 | Crawford | 604/212 |
| 4,578,060 | 3/1986 | Huck et al. | 604/133 |

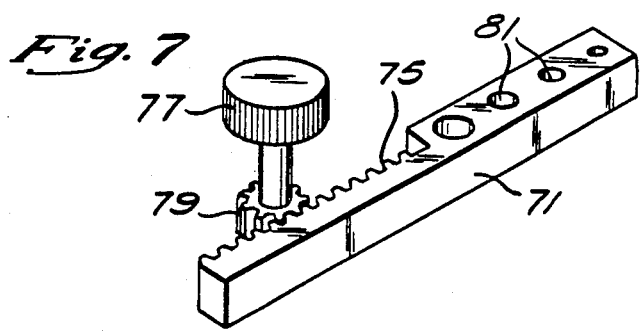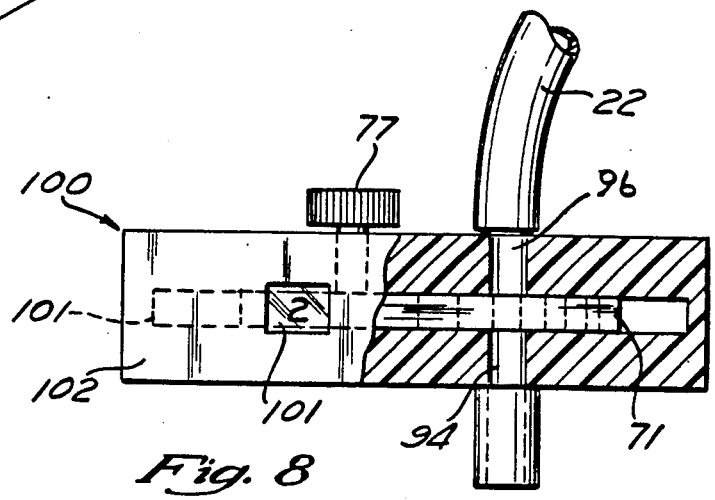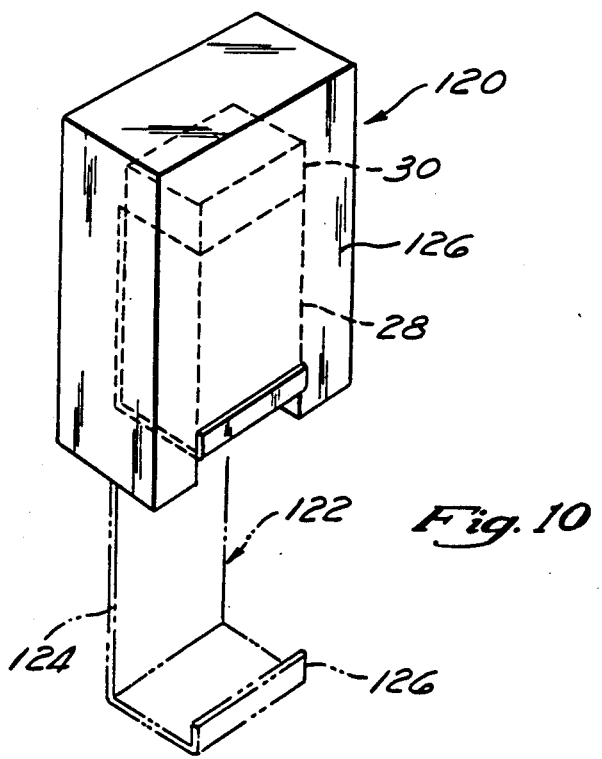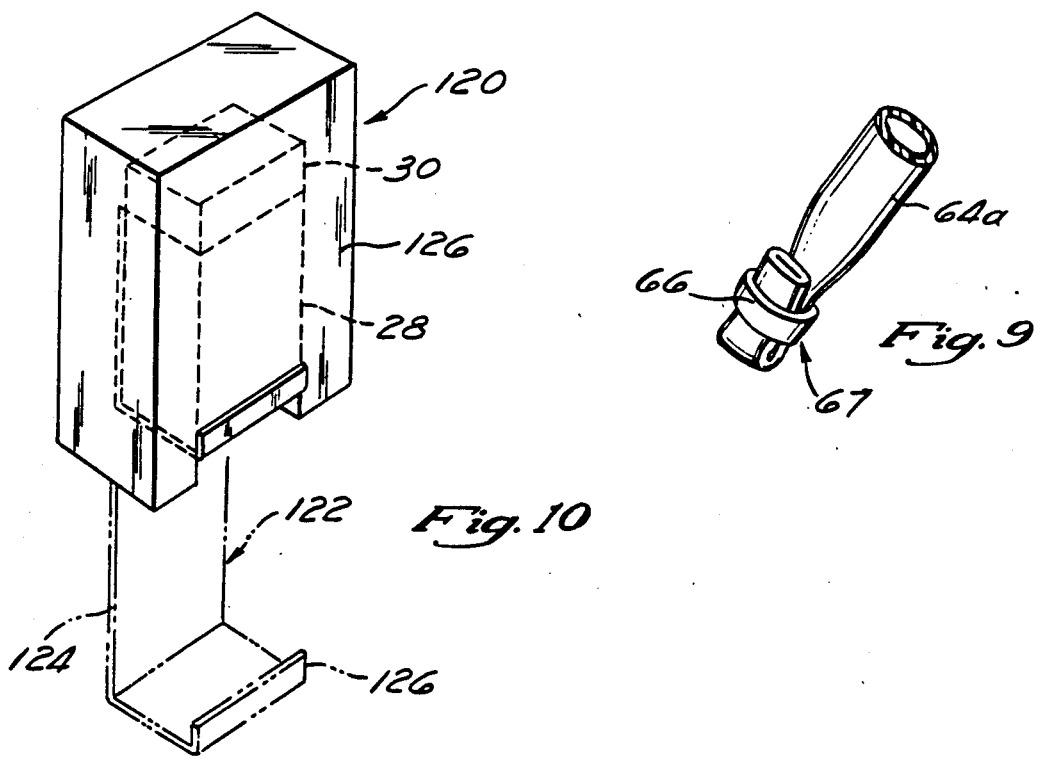

PRESSURIZED FLUID DISPENSER

BACKGROUND OF THE INVENTION

This invention relates generally to pressurized fluid dispensers and more specifically, to pressurized fluid dispensers using an elastic bladder to pressurize the contents.

One application for a bladder-type dispenser is for injecting liquid medications and other fluids into the human body. When injecting fluids into the human body, generally a certain flow rate is prescribed by a physician. Presently a drop counter is used to accomplish this task. Drop counters typically comprise a bottle having a medication in fluid form, which is hung at a height above the patient. The flow rate is adjusted by adjusting a flow control valve until the appropriate number of drops pass out of the valve over a period of time.

The drop counter apparatus for dispensing fluids has several shortcomings. The most prominent shortcoming is inaccuracy in the flow rate of the fluid into the body. The bottle can be hung at various heights in relation to the body and, as the bottle empties, the level of the fluid in the bottle changes. Both of these factors change the total head of the system, which, in turn, changes the flow rate of the system. In addition, different surface tension and viscosity are associated with each fluid. The surface tension and viscosity determine the size of the drops formed by the fluid. The variation in total head and the different sizes of drops can result in inaccuracies of 15 to 20% above or below the prescribed flow rate at any given time.

Drop counters also have other disadvantages in both field and hospital applications. Whenever a patient has to be moved the drop counter must also be moved. Often, an additional person must carry the bottle of fluid or medication during the patient's transport.

Because of the inaccuracies associated with the drop counters, other means have been used in an attempt to inject liquid medications into the body. Pumps increase the accuracy of the flow rate of fluid into the body; however, the motion of the fluid as it is pumped interferes with the systolic motion of the blood stream. In other words, a pump injects fluid at an uneven flow rate.

Pressurizing the fluid has been looked to as a solution. However, prior art attempts at pressurization have met with problems as well. Gas cannot be used with the fluid, since the gas and fluid may react with each other, and it is vitally important that the medication not react with other substances. Furthermore, gas pressurization also runs the risk of inadvertently injecting gas into a person's body, which can be fatal.

Pressurization by use of an expandable bladder has been attempted in the past but has encountered problems. A prominent problem of the previous attempts to use a bladder has been a variation in flow rates as the bladder nears the empty condition. The pressure drops drastically as the bladder empties and, as a result, the flow rate also drops. Several of the prior art devices have attempted to address this problem; however, they have had limited success.

The present inventor is also among the inventors of several of the prior art devices using bladders. The device disclosed in U.S. Pat. No. 3,506,005, and an improvement on that device disclosed in U.S. Pat. No. 3,698,595, both of which were co-invented by the present inventor, use a bladder mounted axially on a mandrel. These devices not only require a specially manufactured bladder but also are difficult to assemble since mounting the bladder on a mandrel requires tedious alignment of the bladder with the mandrel. The valve mechanism necessary to control the flow rate out of the bladder in those devices is also very complex. The valve requires a number of specially manufactured parts and also uses a metal spring to maintain the valve in a closed position. The metal spring is not isolated from the fluid and thus a chemical reaction, such as oxidation, may alter the fluid flowing past the spring. Furthermore, the valve allows variation in the flow rates as the pressure drops.

The device disclosed in U.S. Pat. No. 3,907,169, of which the present inventor was also a co-inventor, uses a bladder mounted on the outside surface of a pivoting curved spatulate member. This device eliminates the difficulties of aligning the bladder upon a mandrel during manufacture; however, the pivoting of the spatulate member causes other problems. Since the spatulate member can move as the bladder is filled or emptied, the bladder must be attached to the spatulate member. The bladder has to be specially formed to accommodate specially formed clips for attaching the bladder to the spatulate member. The devices uses a complex valve similar to that disclosed in the previous patents. The problems associated with the valve in the prior patents are also associated with the device described in this patent.

Thus, there has been a need for a bladder-type dispenser that can pressurize a fluid and maintain a substantially constant flow rate as the bladder empties, is easily manufactured and assembled, and is easy to use. In addition, there is a need for a valve system on a bladder-type dispenser having simple, reliable operation and having no metal components in contact with the fluid inside the dispenser.

SUMMARY OF THE INVENTION

The bladder-type dispenser of the present invention cures the shortcomings discussed above. The bladder-type dispenser comprisess a bladder having an open end and a closed end, which is and made of an elastomeric material. The dispenser also includes a bladder mounting structure including a fixed structural member having a convex curved surface and mounting elements for fixing the two ends of the bladder in relation to the curved surface, so that the bladder is stretched along that curved surface.

The bladder is preferably an essentially tubular length of elastomeric material, which may be extruded or molded. The bladder preferably includes an enlarged portion at the closed end. The bladder mounting element for fixing the closed end includes a slot for receiving this enlarged portion of the bladder.

The fluid dispenser also includes a flow controller for regulating the flow of fluid out of the bladder. The flow controller is preferably separate from the bladder and the bladder mounting structure, and may be removably attached thereto. The flow controller includes a body having a fluid passage through it including an inlet passage and an outlet passage. The block additionally has a cavity formed in it so that a portion of the cavity forms a segment of the fluid flow passage between the inlet passage and the outlet passage. A shutoff element is contained in the cavity and is movable therein to vary the cross sectional flow area of the fluid passage through the cavity. The control for the movement of the shutoff element is outside the fluid flow passage so the fluid being dispensed does not contact the control mechanism.

BRIEF DESCRIPTION OF THE DRAWINGS

FIG. 7 is a perspective view of the gear-actuated plate as an alternative flow controller for use in the fluid dispenser of the invention;

FIG. 8 is a plan view of the alternative flow controller;

FIG. 9 is a view of the closed end of an alternative embodiment of the bladder useful in the dispenser of the invention; and FIG. 10 is a perspective view of a removable mounting for the bladder-type dispenser.

DESCRIPTION OF THE PREFERRED EMBODIMENT

Figure 1:
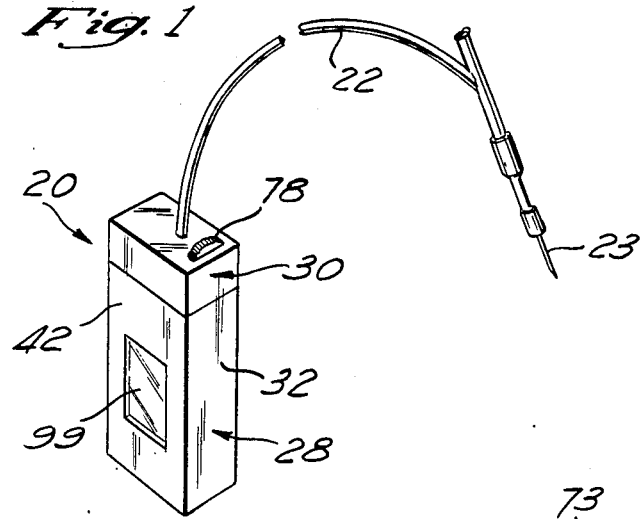
FIG. 1 is a perspective view of the assembled bladder-type dispenser of the invention.

Referring to FIG. 1, the bladder-type dispenser 20 is shown as it would be typically used. A line 22 of microbore tubing connects an outlet of the bladder-type dispenser 20 and an injection needle 23. The needle 23 may be inserted in a patient's body. Liquid medication passes through the tubing 22 and the needle 23 into the patient. Nevertheless, dispensing medications into the human body is just one possible use of the bladder-type dispenser 20 of the invention. The bladder-type dispenser of the invention may also be used to dispense a variety of other liquid substances, including industrial chemicals, foodstuffs, or cosmetics in industrial and consumer applications.

Figure 2:
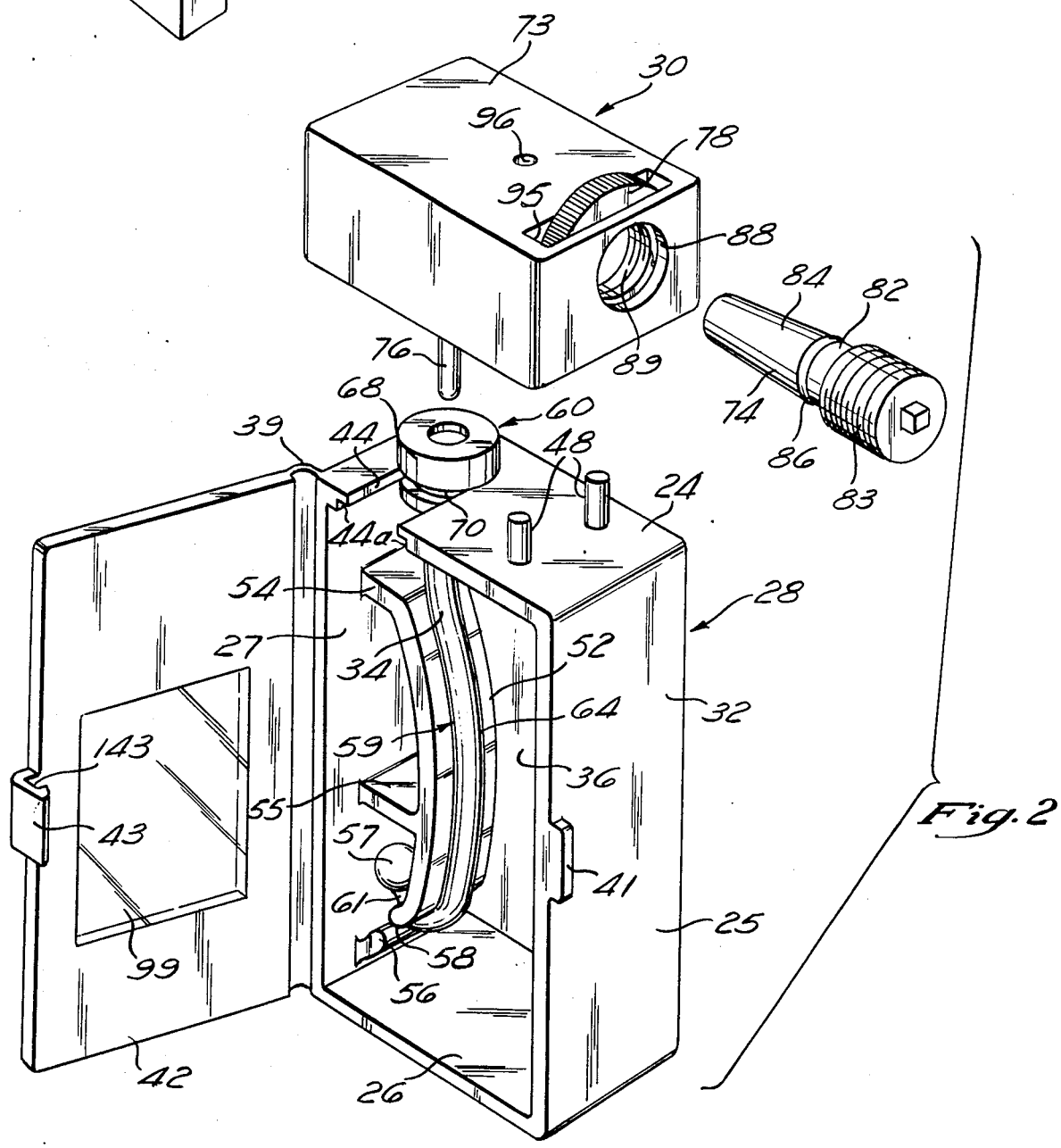
FIG. 2 is an exploded perspective view of the bladder-type dispenser of the invention, with the door opened to show the bladder in its prestressed, empty state.

Referring to FIGS. 1 and 2, the bladder-type dispenser 20 comprises a bladder cassette 28 and a mating flow controller 30. The bladder cassette 28 comprises a main housing 32, a cover 42, and a bladder assembly 59.

THE BLADDER HOUSING

In the preferred embodiment of the bladder cassette 28, the main housing 32 is a substantially rectangular box. The housing 32 comprises a substantially rectangular back 36 with four rectangular sidewalls 24, 25, 26, and 27, attached at right angles along the four edges of the back 36. Attached to the free edge of the sidewall 27 is a hinged cover 42. The substantially rectangular cover 42 is dimensioned to fit atop the main housing 32 to form a closed container. A thin, flexible plastic hinge 39 preferably connects the cover 42 to the sidewall 27. The cover 42 is held closed by a latch 43. A lip 41 on the outer edge of the opposite sidewall 25, and at right angles to that sidewall 25, engages the flexible locking tooth 43 on the long free edge of the cover 42. The locking tooth 43 is positioned on the cover 42 so that a notch 143 in the locking tooth 43 engages the lip 41 on the main housing 32.

It is apparent to one skilled in the art that a number of other arrangements for attaching the cover 42 to the housing 32 can be used. For example, a sliding cover could replace the hinged cover 42. The hinge 39 and lock 43 of the preferred embodiment would be replaced with a set of grooves in the sidewalls 24, 25, 26, 27 to receive a sliding cover. For example, the bottom sidewall 26 can be provided with a slot spaced a small distance from its free edge and extending across the width of the housing. On each adjoining sidewall 25, 27 would be a groove aligning with that slot. A similar groove in the top sidewall 24 would align with the grooves in the sidewalls 25, 27. The cover of that embodiment would be essentially rectangular and dimensioned to fit snugly within grooves in the sidewalls 24, 25, 27 and the slit in the bottom sidewall 26. When the cover is fully inserted a box-like container or cassette 28 is formed.

The top sidewall 24 of the main housing has a first valve structure mounting portion 44 for firmly holding the top portion of the bladder assembly 59. The preferred mounting is a U-shaped opening 44 extending from the free edge of the top sidewall 24 toward the back 36. The U-shaped opening 44 passes through about three-fourths of the front-to-back width of the top sidewall 24. The opening 44 is located near one corner of the box-like container. Around the perimeter of the opening 44 on the interior face of the top sidewall 24 is an undercut 44a.

Located on the exterior surface of the top sidewall 24 are preferably a pair of vertical aligning pins 48. The aligning pins 48 are preferably located about half-way between the U-shaped opening 44 and the most distant short edge of sidewall 24. The pins 48 are preferably cylindrical in shape. To provide for solid placement of the alignment pins 48, a reinforcing block (not shown) is preferably attached to the interior surface of the sidewall 24 opposite the pins 48.

Extending into the interior of the main housing 32 and along the interior surface of the sidewall 27 is a fixed structural element, 34, one side of which forms a convex curved prestressing surface 52. The prestressing structural element 34 has a first end 54 and a second end 56. The prestressing surface 52 is approximately the length of the sidewall 27 and is convex to the sidewall 27. The first end 54 of the prestressing element 34 is firmly attached to the interior surface of the sidewall 27 near the top of the housing 32. The second end 56 of the prestressing element 34 may be attached to the interior of the sidewall 27. Preferably the prestressing surface 52 is integrally formed with the housing 32. For added structural integrity a support member 55 may be connected between the sidewall 27 and the prestressing surface 52 a short distance from the second end 56. The prestressing element 34 may be connected along its length to the back 36 of the housing 32.

The prestressing structural element 34 preferably extends relatively near the sidewall 27 so as to take up a minimum of space in the interior of the housing 32. The convex curved prestressing surface 52 has its top end substantially in vertical alignment with the first, valve element mounting 44.

A second bladder mounting 58 is located near the second end 56 of the curved prestressing surface 52, the end remote from the valve assembly mounting 44. The second bladder mounting 58 receives the closed end of the bladder 64. A slot 58 is preferably formed in the prestressing element 34 near its second end 56. This slot 58 may extend across the full width of the prestressing element 34. The edges of the prestressing element 34 at the slot 58 are rounded to prevent damage to the bladder. Alternatively, the lower end 56 of the prestressing element 34 may terminate a short distance from the sidewall 27, leaving a space forming the slot 58 between the lower end 56 of the prestressing element 34 and the sidewall 27.

THE BLADDER ASSEMBLY

Figure 4:
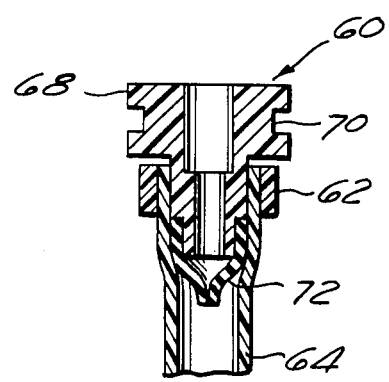
FIG. 4 is a cross-sectional view of the valve mounting element and valve of the bladder.

The bladder assembly 59 is positioned within the main housing 32, as shown in FIG. 2. Referring to FIGS. 2 and 4, the bladder assembly 59 comprises a valve mounting element 60, a locking element 62, a valve 72, and a molded or extruded elastomeric bladder 64.

The valve mounting element 60 holds the bladder 64 securely, and provides for the valve 72 for controlling the flow of fluid into and out of the bladder 64. The valve mounting element 60 also holds the top end of the bladder assembly 59 firmly to the top sidewall 24 of the main housing 32 by interaction with the valve assembly mounting 44. The valve mounting element 60 is shaped to fit snugly into the U-shaped opening 44 in the top sidewall 24 of the housing 32, as shown in FIG. 2.

Referring now to FIG. 4, the preferred form of the valve mounting element 60 is shown. The mounting element is generally tubular in shape, with a wide, grooved flange 68 on one end. The opening passing through the mounting element 60 may have two different inside diameters. A ledge is formed where the diameter of the opening changes. An annular groove 70 is centered on the flange 68. The depth of the groove 70 is preferably uniform. The outer diameter of the groove 70 is just slightly less than the width of the U-shaped opening 44 in the housing 32, while the outer diameter of the flange 68 is greater than the width of the opening 44. The axial width of the groove 70 is also slightly greater than the thickness of the top sidewall 24 of the housing 32 less the undercut 44a, so the lower rail of the flange 68 fits into the undercut 44a. The dimension differences between flange 68 and its groove 70 of the valve mounting element 60, and the U-shaped opening 44 are small so the flange 68 of the mounting element 60 snugly engages the opening 44 to hold the top of the bladder assembly firmly in place.

Located on the end of the mounting element 60 is a valve 72, such as a duckbill valve, which is known in the art. The two flaps of the duckbill valve 72 point away from the flange 68 of the mounting element 60. The flaps can be separated when an elongate member, such as a tube, is inserted through the valve in the direction of the flaps. When the valve 72 is so opened, fluid can pass into or out of the bladder 64. Until such an elongate member opens the duckbill valve 72 the pressure of the fluid in a full bladder 64 holds the flaps of the valve together, preventing passage of any fluid from the bladder.

Other apparatus can be used to prevent the flow of fluid through the valve housing 60 prior to its desired use, while still allowing easy opening when desired. For example, an elastomeric disk of self-sealing, rubber-like material can be used in place of the duckbill valve.

The valve 72 is positioned adjacent the lower edge of the mounting element 60, with a short extension of the mounting element 60 and its central opening extending into the valve, and forming a ledge against which the valve 72 may seat firmly.

The molded or extruded elastomeric bladder 64 is tubular in shape with an open end and a closed end at the closed end is an enlarged portion 57. The embodiment of the bladder 64 shown in FIG. 2 is molded with a closed end forming a necked-down portion 61 and an enlarged solid ball end 57. The necked-down portion 61 and enlarged ball end 57 of this embodiment of the bladder 64 are seen in greater detail in FIG. 5.

An alternative embodiment of the bladder 64a, shown in FIG. 9, is molded or extruded as a straight tube. After the tube is cut to the appropriate length, one end of the tube is folded over and held firmly with a clamp 66 to close off the end of the tube, forming the closed end of the tube with an enlarged portion 67.

The locking element 62 of the valve mounting element 60 of the preferred embodiment (FIG. 4) is preferably a thin-walled plastic clamp having a set of interlocking teeth. After the open end of the bladder 64 is stretched over the smaller end of the mounting element 60 the locking element 62 is clamped on, over the open end of bladder 64. The unflanged end of the mounting element 60 and the locking ring 62 sandwich the open end of bladder 64 to provide a tight seal and a snug fit between the bladder 64 and the mounting element 60. In some instances it may be desired to have the section of the mounting element 60 around which the clamp 62 is placed be slightly longer in the axial direction than the width of the clamp 62, and to provide a slight flare or rim on the end of the mounting element so the clamp 62 clamps down on a neck of smaller diameter than the end of the valve mounting element to provide added security against the bladder 64 slipping off the mounting element.

The bladder's unstressed length is less than the distance from the valve mounting element 60, when attached at the first mounting 44, over the prestressing surface 52 to the second mounting 58, so the bladder is stretched when the valve assembly 60 is attached to the valve mounting 44 and the closed end is attached to the second mounting 58, a will be discussed below.

ASSEMBLY OF THE BLADDER CASSETTE

Figure 5:
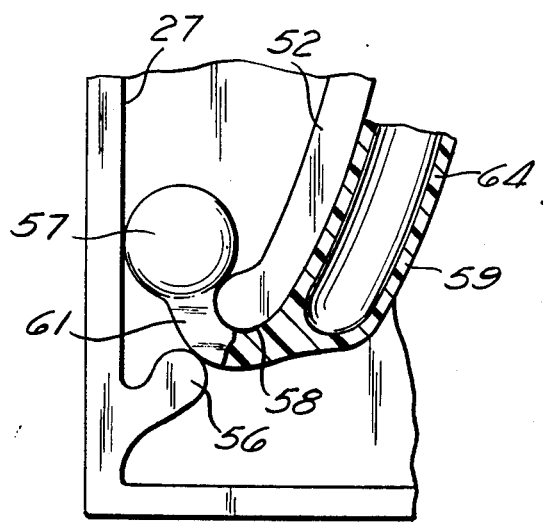
FIG. 5 is a view, partially in cross-section showing the attachment of one embodiment of the bladder onto the prestressing surface.

Assembly of the bladder cassette 28 will now be explained. The bladder assembly 59 is placed in the housing 32. The enlarged end 57 of the bladder 64 is placed in the space between the prestressing surface 52 and the sidewall 27, as shown in FIG. 5. The necked-down portion 61 of the bladder 64 passes through the slot 58. The slot 58 is sufficiently narrow to prevent the enlarged end 57 of the bladder 64 from passing through slot 58. The edges of the slot 58 in the prestressing surface 52 are rounded to prevent tearing of necked down portion 61 of the bladder itself. The bladder 64 is then stretched over the smooth, convex curved prestressing surface 52 and the mounting element 60 is engaged with the U-shaped opening 44. When both ends of the bladder assembly 59 are fixed in the housing 32, the bladder 64 is stretched along the prestressing surface 52, and the bladder 64 is stressed under tension. The curve of the prestressing surface is such that the stretched bladder 64 follows the surface closely and smoothly.

The groove 70 on the flange 68 of the mounting element 60 snugly engages opening 44, and the resilient, elastomeric material of the bladder 64 produces a force normal to the top sidewall 24 to pull the upper rail of the flange 68 firmly against the top sidewall 24. The slot 58 near the second end of the prestressing member firmly holds the closed end of the bladder. The normal force produces a friction force to secure the mounting element 60 and the sidewall 24. After the bladder assembly 59 is mounted within the main housing 32, the cover 42 is closed to complete the cassette 28.

When the alternative bladder shown in FIG. 9 is used, the assembly is generally the same. The enlarged end 67 of the bladder formed by folding over and clamping the end of the bladder tubing is inserted in the space between the prestressing surface 52 and the sidewall 27. A section of bladder tubing adjacent the enlarged end 67 is placed in the slot 58. Again, the enlarged end 67 of the bladder is too large to pass through the slot 58, so the closed end of the bladder 64a is held firmly adjacent the lower end 56 of the prestressing surface 52. The valve end of the bladder assembly 59 incorporating this alternative bladder 64a is identical to that shown and described above, and the attachment of it to the housing 32 is as described above.

The stretching of the empty bladder 64 stresses its walls so as to place its fluid contents under pressure even when there is little fluid in the bladder. This pressure in the nearly empty bladder helps to ensure a smooth, even flow of fluid when the bladder is coupled to an appropriate flow controller 30. The amount of prestressing, and thus the pressure imposed on the fluid to eject it as the bladder nears empty, can be varied by using bladders of different length. A shorter bladder will be under greater tension when it is stretched over the curved prestressing surface 52 than a longer bladder. This greater tension will translate into greater pressure of the fluid in the bladder.

The bladder 64 is sufficiently elastic that it does not rupture when it is so stretched, or when it is further stressed by filling with fluid. Preferably the bladder 64 should be sufficiently elastic that it can be filled to the point at which the bladder occupies virtually the entire interior of the cassette housing 32, except for the portion between the prestressing surface 52 and the sidewall 27.

THE FLOW CONTROLLER

The flow controller 30 is removably attached to the top of the bladder cassette 28 to open the valve 72 and to regulate the flow of fluid from the bladder 64 into the flow tube 22.

Figure 3:
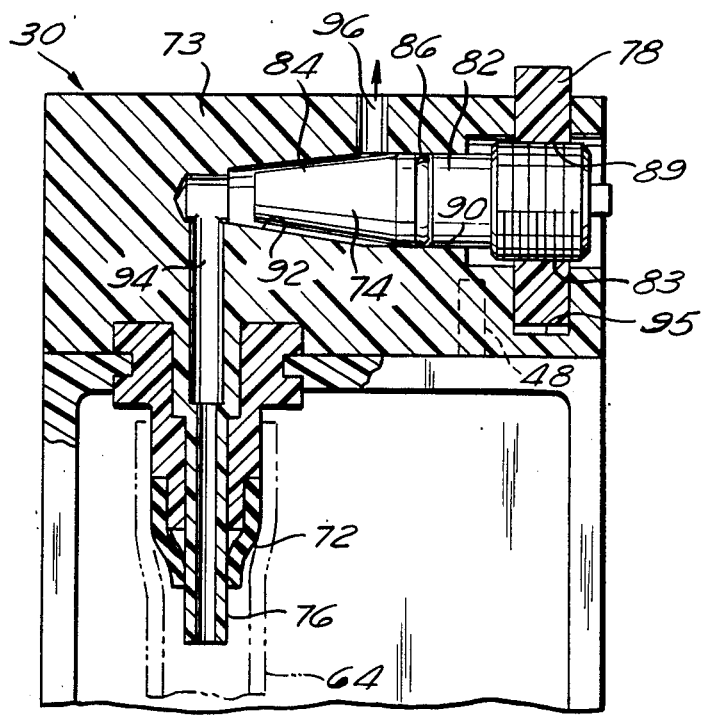
FIG. 3 is a cross-sectional view of one embodiment of the flow controller of the dispenser of the invention.

Referring to FIGS. 2 and 3, the flow controller 30 comprises a block 73 having an opening or cavity 88 in it. The block 73 additionally includes a fluid passage through it comprising an inlet passage 94, an outlet passage 96, and a portion of the cavity 88. A shutoff element 74 fits into the opening 88, a probe 76 is connected at the end of the inlet fluid passage 94, and a control mechanism 78 controls the shutoff element 74. The shutoff element moves within the cavity 88 to control the cross sectional flow area of the fluid flow path through the cavity 88 from the inlet passage 94 to the outlet passage 96.

The control mechanism 78 is sealed from the fluid passage from the inlet passage 94 to the outlet passage 96 by sealing the shutoff element 74 in the cavity 88 so fluid flowing through the portion of the cavity 88 from the inlet 94 to the outlet 96 does not flow around the shutoff element 74 to the control mechanism. Thus, the control for the shutoff is provided outside the fluid flow passage and the fluid being dispensed does not contact the control mechanism.

The preferred shutoff element 74 includes a cylindrical portion 82 and a frusto-conical end portion 84. The larger base of the frusto-conical portion 84 abuts the cylindrical portion 82. On the cylindrical portion 82, near the joint with the larger base of the frusto-conical end 84 is a shallow annular groove carrying a seal 86. The remaining exterior surface of the cylindrical portion 82 has outside threads 83.

The opening 88 extends to one end of block 73 in this preferred embodiment of the flow controller. The shape of opening 88 in the block 73 corresponds to the shape of the shutoff element 74. The opening 88 has a cylindrical portion 90 (FIG. 3) and a frusto-conical portion 92. The cylindrical portion 90 of the opening 88 extends through the block 73 to one of the end faces.

The fluid passage through the block 73 has an inlet opening 94 and an outlet opening 96 in the block 73. One end of the inlet passage 94 opens into the frusto conical portion 92 of the opening 88. The other end of the inlet passage 94 extends to one of the large rectangular faces of block 73. The outlet opening 96 extends from the frusto-conical portion 92 of the block opening 88 to the face of the block 73 opposite the face having the inlet opening 94.

The shutoff element 74 fits into the opening 88 as shown in FIG. 3. When installed, the frusto-conical portion 84 of the shutoff 74 fits into the frusto-conical portion 92 of the cavity 88, and the cylindrical portion 82 of the shutoff 74 fits into the cylindrical portion 90 of the block opening 88. The O-ring seal 86 fits tightly between the shutoff 74 and the walls of the opening 88 to provide a fluid seal to prevent fluid from leaking out through the opening 88 around the shutoff element 74. The seal 86 is positioned on the shutoff element 74 so that when the shutoff 74 is in its innermost position the seal 86 is outward of the outlet passage 96, so it is not in the fluid passage between the inlet opening 94 and the outlet opening 96. This seal 86 seals the control mechanism from the fluid flow passage.

A probe 76 extends coaxially from the inlet opening 94. The probe 76 can either be a tubular piece of acceptable medical grade material or a spike, both of which are known in the art. A tubular piece of medical grade material would be used in conjunction with a duckbill valve attached to the mounting structure 60. A spike may be used when a disk of self-sealing rubber-like material is substituted for the duckbill valve. The end of the probe 76 contacting the inlet 94 may be flared outward slightly to wedge the probe 76 in the opening of the valve mounting structure 60 and seal the flow path through the flow controller 30.

A flow restrictor (not shown) may be fitted within the inlet opening 94. Such a flow restrictor produces an opening that varies in size in response to the pressure of the fluid in the bladder 64. The flow restrictor may constrict the opening to produce a smaller opening and reduce the amount of fluid flow at higher pressures. As the fluid pressure in the bladder 64 drops, the opening of the flow restrictor gets larger. The pressure responsive flow restrictor evens out the flow rate of the fluid coming from the bladder 64. Thus, the flow rate of the fluid stays substantially constant until the bladder 64 is essentially empty. A flow restrictor having a fixed orifice may also be used to obtain similar results in some situations.

Fluid flow through the flow controller 30 by flowing through the probe 76, into the inlet passage 94, through the frusto-conical portion 92 of the opening 88 past the frusto-conical portion 84 of the shutoff element 74, and then through the outlet passage 96. The O-ring seal 86 on the cylindrical portion 82 of the shutoff element 74 prevents the fluid from flowing past the shutoff element 74 to the position control mechanism and through the open end of the opening 88.

The axial position of the shutoff element 74 within the block opening 88 is adjustable to control the amount of fluid that flows from the inlet passage 94 to the outlet passage 96. When the shutoff 74 is at its extreme innermost position, the frusto-conical portion 84 of the shutoff seats snugly against the frusto-conical portion 92 of the opening 88, and no fluid can flow around the frusto-conical portion of the shutoff from the inlet passage 94 to the outlet passage 96. As the shutoff 74 is moved axially outward, a small gap develops between the frusto-conical portion of the shutoff and the walls of the opening 88, allowing a small amount of fluid to flow past the shutoff from the inlet passage 94 to the outlet passage 96. As the shutoff 74 is moved farther out, the gap between the shutoff and the opening walls widens, allowing a greater amount of fluid to flow through the cavity portion between the inlet and outlet passages of the flow controller 30. Changing the axial position of the shutoff 74 in the opening 88 varies the cross-sectional area of the flow path. The flow rate of fluid through the flow controller 30 varies as the cross-sectional area of the flow path varies.

The position of the shutoff element 74 in the block opening 88 is controlled by the control knob 78, which threadably engages the cylindrical portion 82 of the shutoff element 74.

The thumb control 78 is fitted within a slot 95 in the block 73. The slot 95 is open on the top, but is preferably closed on the bottom. The thumb control 78 includes a plastic disk dimensioned to fit within the slot 95, and has a central threaded opening. The threads 89 on the central opening of the control knob 78 match the threads 84 on the outer surface of the cylindrical portion 82 of the shutoff element 74. The control knob 78 is knurled on the outside perimeter so a person can easily turn it with his finger or thumb.

When the control disk 78 is rotated, the threads 89 on the disk 78 engage the threads 83 on the shutoff 74 to move the shutoff 74 into or out of the opening 88 to vary the fluid flow rate through the flow controller 30. When the desired flow rate is achieved, the threads 89 on the control disk 78 and shutoff 74 help maintain the position of the cylindrical portion of the shutoff 74. The threads 83, 89 are sealed from the fluid flow path by the seal 86 around the perimeter of the shutoff element 74, axially between the frusto-conical portion 84 and the threads 83.

The opening 88 in the block 73 is positioned nearer one face of the block 73 so that thumb control knob 78 in the slot 95, which is centered on the axis of the opening 88, is exposed through the top of the slot 95. Thus, when an adjustment of the flow rate is needed, the disk 78 can be easily rotated by a person's thumb or finger.

In some applications it may be desirable to provide a fixed, predetermined flow rate. In such situations, a stationary shutoff 74 eliminates error on the part of the user or medical personnel. The flow rate is predetermined for the particular medication and the position of the shutoff 74 is fixed in the cavity 88 to provide that fluid flow rate, and the user-adjustable control knob 78 becomes unnecessary.

Referring to FIG. 3, two openings are located on the rectangular surface of the block 73 having the inlet opening 94. These openings fit with the alignment pins 48 on the top of the cassette housing 32. The two preferably cylindrical openings have inside diameters slightly larger than the outside diameters of the aligning pins 48, and the distance between the centers of the openings is the same as the distance between the centers of the aligning pins 48.

ATTACHING THE FLOW CONTROLLER TO THE BLADDER CASSETTE

In assembly by the flow controller 30 and the bladder cassette 28, the aligning pins 48 are inserted into the openings in the block 73 while the probe 76 is inserted through the valve 72 in the valve attachment 60. The probe 76 thus opens the valve 72. The probe 76 and two pins 48 should be parallel to ensure that the flow controller 30 will align with the cassette 28 during connection. After the flow controller 30 is placed on the cassette 28, the probe 76 extends past the duck bill valve 72 and into bladder 64.

The outlet passage 96 of the flow controller is connected to micro bore tubing, such as is known in the art, which serves as the line 22 to the patient (FIG. 1). The pressure of the fluid in the bladder 64 forces fluid through the flow controller 30, the outlet 96 and the dispensing conduit, such as the line 22 and the needle 23.

USE OF THE FLUID DISPENSER

Advantageously, the bladder 64 is filled while in the cassette 28. The flow controller 30 is not needed to fill the bladder 64. This allows the multiple bladder cassettes 28 to be filled at a remote location and used interchangeably with one flow controller 30.

The bladder 64 is filled after the bladder assembly 59 is positioned within the main housing 32 and the cover 42 is locked into place with the lip 41 and the locking tooth 43. The bladder 64 is filled with an instrument such as a syringe or commercially available filling machine such as are presently in use in hospital pharmacies, capable of producing a large pressure in the bladder 64. A probe such as the flow controller probe 76 is mounted on the syringe. The probe is passed through the duckbill valve 72 or self-sealing rubber-like disk and the medical fluid is inserted into the bladder 64. When the bladder 64 is full, the instrument is removed and the duckbill valve or self-sealing rubber-like disk closes, preventing the outward flow of the fluid. With a full bladder 64, the cassette 28 can be attached to the flow controller 30 with the aligning pins 48 and the spike or probe 76 for use.

The flow controller 30 and the cassette 28 are two separate parts that form an interchangeable system. Thus, only a limited number of flow controllers 30 needs to be kept on hand, which can be used with any bladder cassette 28 of a particular size. With the bladder cassette 28 and the flow controller 30 interchangeable, a user's stocking requirements are simplified.

The cover 42 of the housing 32 preferably includes a window 99 (see FIGS. 1 and 2) to allow observation of the bladder 64 as it empties. The interior surface of the back 36 of the cassette housing 32, opposite the window 99, may be marked with graduations to indicate the quantity of fluid remaining in the bladder 64. In the preferred embodiment, the various graduations are colored to further aid personnel in observing the bladder status as it empties.

ALTERNATIVE FLOW CONTROLLER

Referring to FIGS. 7 and 8, an alternative apparatus for controlling the flow rate through the flow controller is shown. The shutoff element 74 and control knob 78 of the preferred embodiment regulating the flow between the inlet passage 94 and the outlet passage 96 are replaced by a shutoff element 71 providing rack and pinion control to align one of a plurality of separate, distinct flow openings 81 for connecting the inlet and outlet passages 94, 96 of this flow controller 100 to change to cross-sectional flow area of the fluid passage through the controller.

For this embodiment the inlet passage 94 and outlet passage 96 of the flow controller 100 are axially aligned on opposite sides of a perpendicular elongate opening or cavity 101 in the block 102 housing the flow controller 100. An elongate rack 71 have a toothed segment and an opening segment is contained within the elongate cavity 101.

The opening segment of the elongate rack 71 has a plurality of openings 81 through it of distinct sizes. Each of these openings 81 may be moved into alignment between the inlet passage 94 and the outlet passage 96 of the flow controller block by longitudinally moving the elongate rack 71 within the block opening.

The movement of the rack 71 is accomplished by the interaction of the teeth 75 of the toothed segment of the rack 71 and the pivoting pinion 79 and knob 77. The knob 77 projects outside the block 102 of the flow controller 100 so the user has access to it to turn it. The knob 77 rotates in one location in block 102, while the rack 71 moves within the opening 101. Adjustment of the rate of fluid flow from the flow controller's inlet passage 94 to the outlet passage 96 is provided by turning the knob 77. When the knob 77 is turned, the teeth of the pinion 79 engage the teeth 75 of the rack 71 to move the rack 71 longitudinally until the proper opening 81 is aligned between the inlet and outlet passages 94, 96.

The openings 81 in the rack 71 are spaced so only one opening aligns with the flow path at any given time. Flow is shut off when the rack 71 is positioned so the inlet and outlet passages are between openings 81 in the rack 71 by a set of seals, one around the inlet opening and another around the outlet opening. These seals also ensure that when one opening 81 is selected fluid does not seep around the shutoff element 71 to flow through others of the openings 81, thus yielding a different flow rate than desired. Further, the control mechanism consisting of the toothed portion 75 of the rack 71 and the pinion 79 are completely outside the fluid flow passage.

Numbers may be spaced along the side of the rack 71 opposite the teeth 75 of the toothed portion. The edge of the block 102 may have a view window 101 through which one number is visible at each position of the rack 71 to indicate which opening 81 is aligned in the fluid flow path. The numbers may correspond to flow volumetric rates associated with each opening 81 in the rack 71.

HOLDERS FOR THE FLUID DISPENSER

Referring to FIG. 10, an apparatus for conveniently aligning and holding the bladder cassette 28 is shown schematically. A holster 120 permanently houses the flow controller 30. The holster 120 has a sliding cradle member 122 having a first, open position, and a second, closed position. the open position of the cradle 122 is shown with phantom lines in FIG. 10. The sliding cradle 122 includes an L-shaped element 124, having an upturned end 126. A bladder cassette 28 fits snugly in the sliding member 122. The cassette 28 can be mounted in the cradle 122 when the holder 122 is in the open position, extended out from the holster body 126. The cassette 28 engages the flow controller 30 when the cradle 122 is moved to the closed position within the holster body 126. The sliding element 122 holds the cassette 28 in correct alignment as it slides into position. The cassette is aligned by virtue of its position in the L-shaped element 124 sliding holder 122. When the bladder in the cassette 28 is empty, the cradle 122 may be slid to the open position, and the cassette 28 removed and replaced.

Figure 6:
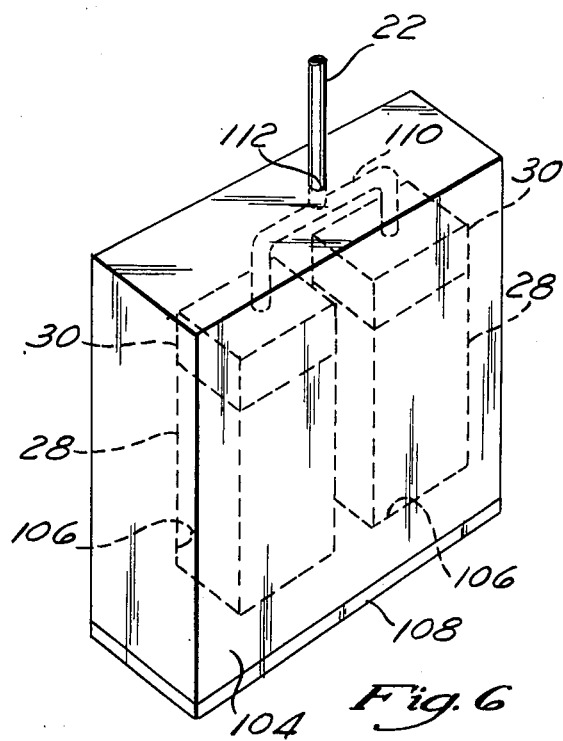
FIG. 6 is a perspective view of a dual flow dispenser constructed according to the invention.

FIG. 6 discloses an apparatus for holding a plurality of bladder cassettes 28 and flow controllers 30. The apparatus includes a holster 104 with a plurality of flow controllers 30 integrally attached to the holster 104. The cassettes 28 are removable, and slide into and out of compartments 106 in the holster 104. A door 108 on the bottom of the holster 104, which may be hinged or sliding, encloses the compartments 106 and holds the cassettes 28 in place during use, while allowing access to change the bladder cassettes 28 when necessary.

The flow controllers have probes 76, such as spikes or tubes of appropriate medical grade material attached to the inlet openings 94. The outlets 96 empty into a mixing chamber 110. The fluids mix and the pressure of the multiple bladders forces the mixture from the holster outlet 112 where the fluid can be injected into a patient.

Although the invention has been described in terms of certain preferred embodiments, modifications will be apparent to those skilled in the art. All such modifications are intended to be included within the scope of the following claims.

I claim:
1. A pressurized fluid dispenser comprising:
an elastic bladder having a closed end and an open end; and
a bladder mounting structure comprising:
   a fixed structural member having a convex curved surface;
   first and second mounting elements for fixing said open and closed ends of said bladder, respectively, in relation to said fixed structural member so that said bladder is stretched along said convex curved surface;
a flow controller in fluid communication with said open end of said bladder, comprising:
   a body block;
   a fluid flow passage through said block, said passage including an inlet passage in fluid communication with said open end of said bladder and an outlet passage;
   a cavity in said body, said fluid flow passage including a portion of said cavity between said inlet passage and said outlet passage;
   a shut-off element contained within said cavity, wherein said shut-off element is moveable within said cavity to vary the cross sectional flow area of said fluid passage through said cavity, and wherein control for the movement of said shut-off element is provided outside said fluid passage, said shut-off element comprising:

a rack having a toothed portion and an opening portion including a plurality of openings, wherein said rack is moveable within said cavity to selectively bring each of said openings into alignment with said inlet passage and said outlet passage; and a pinion engaging said toothed portion of said rack, wherein rotation of said pinion causes said rack to move within said cavity.

2. A device for dispensing a fluid, comprising:

a bladder assembly comprising:
   a substantial tubular length of elastomeric material having an open end and a closed end forming a bladder;
   a self-closing valve assembly, said valve assembly in fluid communication with said open end of said length of elastomeric material;
   a main housing to which said valve assembly is attached, having a fixed, curved surface, wherein said closed end of said length of elastomeric materials is fixedly attached adjacent one end of said curved surface, and wherein said valve assembly of said bladder assembly is fixedly attached to said main housing near the other end of said curved surface, so that said length of elastomeric material is stretched over said curved surface for pressurizing said fluid;

a flow controller removably attached to said valve assembly to regulate the flow of fluid out of said bladder, said flow controller comprising a body having a fluid flow path through said body, including an inlet passage and an outlet passage, the flow controller further comprising a probe, said probe coupled to said inlet passage so that as said flow controller is attached to said main housing said probe enters through said valve assembly into the open end of said bladder, thereby opening said valve assembly so long as said flow controller is attached to said main housing, while permitting said valve assembly to close whenever said flow controller is removed from said main housing, said flow controller body further including a cavity, a portion which forms a segment of said fluid flow path, said flow controller further comprising:
   a shut-off element having substantially the same shape as said cavity, wherein said shut-off element is movable within said cavity to adjustably fill said cavity and provide selective amounts of obstruction to said fluid flow path, and wherein a portion of said shut-off element is sealed from said fluid flow path.

3. A device for dispensing a fluid comprising:

a bladder assembly, comprising:
   a substantially tubular length of elastomeric material having an open end and a closed end forming a bladder;
   a valve assembly, said valve assembly in fluid communication with said open end of said length of elastomeric material;
   a main housing having a fixed, curved surface, wherein said closed end of said length of elastomeric materials is fixedly attached adjacent one end of said curved surface, and wherein said valve assembly of said bladder assembly is fixedly attached to said main housing near the other end of said curved surface, so that said length of elastomeric material is stretched over said curved surface;

a flow controller removably attached to said valve assembly to regulate the flow of fluid out of said bladder, said flow controller further comprising a body having a fluid flow path through said body, including an inlet passage and an outlet passage, the flow controller further comprising a probe, said probe coupled to said inlet passage so that as said flow controller is attached to said main housing said probe enters through said valve assembly into the open end of said bladder, said flow controller further comprising:
   a rack, said rack having a plurality of openings through said rack, and said rack having a toothed segment; and
   a rotatable cylindrical pinion engaging the toothed segment of said rack, wherein rotation of said pinion causes said rack to move to selectively align one of said rack openings with said flow path through said block.

4. A flow controller for a bladder-type fluid dispenser, the flow controller comprising:
   a body block;
   a fluid flow passage including an inlet passage and an outlet passage through said block;
   a cavity in said body, said fluid flow passage including a portion of said cavity between said inlet passage and said outlet passage;
   a shut-off element contained within said cavity, wherein said shut-off element is moveable within said cavity to vary the cross sectional flow area of said fluid passage through said cavity, wherein control for the movement of said shut-off element is provided by a mechanism sealed from said fluid passage, said shut-off element comprising:
   a rack having a toothed portion and an opening portion including a plurality of openings, wherein said rack is moveable within said cavity to selectively bring each of said openings into alignment with said inlet passage and said outlet passage; and
   a pinion engaging said toothed portion of said rack, wherein rotation of said pinion causes said rack to move within said cavity.

5. A pressurized fluid dispenser comprising:

an elastic bladder having a closed end and an open end;

a housing containing said bladder; and a bladder mounting structure comprising:
   a fixed structural member attached to said housing and having a convex curved surface;
   first and second mounting elements for fixing said open and closed ends of said bladder, respectively, in relation to said fixed structural member so that said bladder is stretched along said convex curved surface;
   a flow controller in fluid communication with said open end of said bladder, comprising:
      a body block;
      a fluid flow passage through said block, said passage including an inlet passage in fluid communication with said open end of said bladder and an outlet passage;
      a cavity in said body, said fluid flow passage including a portion of said cavity between said inlet passage and said outlet passage;
      a shut-off element contained within said cavity, wherein said shut-off element is movable within said cavity to vary the cross-sectional flow area of said fluid passage through said cavity, and wherein control for the movement of said shut-off element is provided outside fluid passage, said shut-off element comprising:
- a rack having a toothed portion and an opening portion including a plurality of openings, wherein said rack is movable within said cavity to selectively bring each of said openings into alignment with said inlet passage and said outlet passage; and
- a pinion engaging said toothed portion of said rack, wherein rotation of said pinion causes said rack to move within said cavity.

6. A device for dispensing a fluid, comprisng:
a bladder assembly, comprising:
- a substantially tubular length of elastomeric material having an open end and a closed end forming a bladder;
- a self sealing valve assembly for preventing fluid from flowing out of said bladder when said valve assembly is closed, said valve assembly in fluid communication with said open end of said length of elastomeric material;
- a main housing including a fixed, curved surface formed integrally therewith, wherein said closed end of said length of elastomeric material is fixedly attached adjacent one end of said curved surface, and wherein said valve assembly of said bladder assembly is fixedly attached to said main housing near the other end of said curved surface, so that said length of elastomeric material is stretched over said curved surface for pressurizing said fluid;
- a flow controller removably attached to said valve assembly to regulate the flow of said fluid out of said bladder, said flow controller comprising a body having a fluid flow path through said body, including an inlet passage and an outlet passage, the flow controller further comprising a hollow probe, said probe coupled to said inlet passage so that as said flow controller is attached to said main housing said probe enters through said valve assembly into the open end of said bladder, thereby holding said valve assembly open so long as said flow controller is attached to said valve assembly, said flow controller body further including a cavity, a portion which forms a segment of said fluid flow path, said flow controller further comprising:
  - a shut-off element having substantially the same shape as said cavity, wherein said shut-off element is movable within said cavity to adjustably fill said cavity and provide selective amounts of obstruction to said fluid flow path, and wherein a portion of said shut-off element is sealed from said fluid flow path.

7. A device for dispensing a fluid comprising;
a bladder assembly, comprising;
- a substantially tubular length of elastomeric material having an open end and a closed end forming a bladder;
- a valve assembly, said valve assembly in fluid communication with said open end of said length of elastomeric material;
- a main housing including a fixed, curved surface formed integrally therewith, wherein said closed end of said length of elastomeric material is fixedly attached adjacent one end of said curved surface, and wherein said valve assembly of said bladder assembly is fixedly attached to said main housing near the other end of said curved surface, so that said length of elastomeric material is stretched over said curved surface;
- a flow controller removably attached to said valve assembly to regulate the flow of fluid out of said bladder, said flow controller comprising a body having a fluid flow path through said body, including an inlet passage and an outlet passage, the flow controller further comprising a probe, said probe coupled to said inlet passage so that as said flow controller is attached to said main housing said probe enters through said valve assembly into the open end of said bladder, said flow controller further comprising;
  - a rack, said rack having a plurality of openings through said rack, and said rack having a toothed segment; and
  - a rotatable cylindrical pinion engaging the toothed segment of said rack, wherein rotation of said pinion causes said rack to move to selectively align one of said rack openings with said flow path through said block.

8. A flow controller for pressurized bladder-type fluid dispenser, said dispenser having a seal for preventing fulid flow out of said dispenser, the flow controller comprising:
- a body block;
- a fluid flow passage including an inlet passage and an outlet passage through said block;
- a cavity in said body, said fluid flow passage including a portion of said cavity between said inlet passage and said outlet passage;
- a shut-off element contained within said cavity in said fluid flow path, wherein said shut-off element is movable within said cavity to vary the cross-sectional flow area of said fluid passage through said cavity, wherein control for the movement of said shut-off element is provided by a mechanism sealed from said fluid passage, said shut-off element comprising a body having a shape substantially identical to a portion of said cavity, wherein said body has an innermost position in which said body fills a portion of said cavity to prevent fluid flow through said cavity from said inlet passage to said outlet passage, and said body is movable from said innermost position, wherein as said body is moved from its innermost position, a fluid passage is opened around said body through said cavity from said inlet passage to said outlet passage; and
- a rigid, hollow probe in fluid communication with said inlet passage extending out from said body, wherein said flow controller is adapted to be removably mounted on said fluid dispenser and said probe is adapted to physically extend through the seal on said dispenser to establish fluid communication between said bladder and said fluid flow passage.

9. The flow controller defined in claim 8, wherein said cavity includes a frusto-conical portion forming said portion between said inlet passage and said outlet passage, and said shutoff body includes a frusto-conical portion shaped to fill said frusto-conical portion of said cavity when said shutoff body is in said innermost position, and said shutoff body is axially moveable from said innermost position so a gap is formed between said shutoff element and the walls of said cavity to permit fluid to flow around said shutoff element body from said inlet passage to said outlet passage, wherein said shutoff body includes a seal around its perimeter at a position not between said inlet and outlet passages, the seal preventing the flow of fluid around said shutoff element body beyond said seal.

10. The flow controller defined in claim 9, wherein:
a portion of said shutoff element body remote from said frusto-conical portion is threaded;
said seal surrounds said shutoff body at a position axially between said frusto-conical portion and said threaded portion; and
said threaded portion of said shutoff element body engages a threaded control knob so that rotation of said control knob moves said shutoff element body axially.

11. A pressurized fluid dispenser, comprising:
an elastic bladder having a closed end and an open end;
a bladder mounting structure, comprising:
a fixed structural member attached to said housing and having a convex curved surface;
first and second mounting elements for fixing said open and closed ends of said bladder, respectively, in relation to said fixed structural member so that said bladder is stretched along said convex curved surface for pressurizing said fluid;
a flow controller adapted to be removably mounted on said housing, comprising:
a body block;
a fluid flow passage through said block, said passage including an inlet passage and an outlet passage;
a cavity in said body, said fluid flow passage including a portion of cavity between said inlet passage and said outlet passage;
a shut-off element contained within said cavity, wherein said shut-off element is movable within said cavity to vary the cross-sectional flow area of said fluid passage through said cavity, and wherein control for the movement of said shut-off element is provided outside said fluid passage, said shut-off element comprising a body having a shape substantially identical to a portion of said cavity, wherein said body has an innermost position in which said body fills a portion of said cavity to prevent fluid flow through said cavity from said inlet passage to said outlet passage, and said body is movable from said innermost position, wherein as said body is moved from its innermost position, a fluid passage is opened around said body through said cavity from said inlet passage to said outlet passage;
means for automatically sealing the open end of said bladder whenever said flow controller is removed from said housing; and
means for automatically establishing fluid communication between said open end of said bladder and said inlet passage whenever said flow controller is mounted on said housing.

12. The dispenser of claim 11, wherein said flow controller cavity includes a frusto-conical portion forming said portion between said inlet passage and said outlet passage, and said shut-off body includes a frusto-conical portion shaped to fill said frusto-conical portion of said cavity when said shut-off body is in said innermost position, and said shut-off body is axially moveable from said innermost position so a gap is formed between said shut-off element and the walls of said cavity to permit fluid to flow around said shut-off element movable within said cavity to adjustably fill said cavity and provide selective amounts of obstruction of said fluid flow path, and wherein a portion of said shut-off element is not in said fluid flow path.

13. The dispenser of claim 12, wherein:
a portion of said shut-off element body remote from said frusto-conical portion is threaded;
said seal surrounds said shut-off body at a position axially between said frusto-conical portion and said threaded portion; and
said threaded portion of said shut-off element body engages a threaded control knob so that rotation of said control knob moves said shut-off element body axially.

* * * * *